United States Patent
Suzuki et al.

[11] Patent Number: 5,814,719
[45] Date of Patent: Sep. 29, 1998

[54] LIMITING CURRENT TYPE OXYGEN SENSOR

[75] Inventors: Takayuki Suzuki; Hozumi Futata, both of Shizuoka; Koji Moriya; Takahiro Sako, both of Osaka; Hideaki Takahashi; Keiichi Saji, both of Aichi, all of Japan

[73] Assignees: Yazaki Corporation, Tokyo; Kabushiki Kaisha Toyota Chuo Kenkyusho, Aichi, both of Japan

[21] Appl. No.: 788,758

[22] Filed: Jan. 24, 1997

[30] Foreign Application Priority Data

Jan. 26, 1996 [JP] Japan ................................. 8-011674

[51] Int. Cl.⁶ .................................................. G01N 27/00
[52] U.S. Cl. ...................... 73/23.31; 73/31.05; 204/426
[58] Field of Search ................................ 73/23.31, 23.32, 73/31.05, 31.06; 204/406, 425, 426

[56] References Cited

U.S. PATENT DOCUMENTS

| | | | |
|---|---|---|---|
| 4,574,264 | 3/1986 | Takahashi et al. | 73/31.06 X |
| 4,595,485 | 6/1986 | Takahashi et al. | |
| 4,661,234 | 4/1987 | Takahashi et al. | 204/406 |
| 5,443,711 | 8/1995 | Kojima et al. | 204/426 X |
| 5,480,535 | 1/1996 | Kondo et al. | 204/425 |
| 5,538,612 | 7/1996 | Kojima et al. | 204/426 X |

FOREIGN PATENT DOCUMENTS

| | | | |
|---|---|---|---|
| 57-076449 | 5/1982 | Japan | 204/426 |
| 61-241657 | 10/1986 | Japan | 73/23.31 |
| 64-004146 | 1/1989 | Japan | 204/426 |
| 2-4858 | 1/1990 | Japan . | |

Primary Examiner—Daniel S. Larkin
Attorney, Agent, or Firm—Sughrue, Mion, Zinn, Macpeak & Seas, PLLC

[57] ABSTRACT

An oxygen sensor of a limiting current type includes a sensing element coated with a porous coating layer having a catalyst supported thereon. The catalyst includes at least one element selected from the group consisting of platinum, rhodium, palladium, iridium and ruthenium, and the content of the catalyst is not more than 50 wt % with respect to the total weight of the porous coating layer, and particles of the catalyst are dispersed within the porous coating layer at spacings of not more than 6 $\mu$m. By using the catalyst, the influence of hydrocarbons to the oxygen concentration is reduced.

5 Claims, 8 Drawing Sheets

LIMITING CURRENT TYPE OXYGEN SENSOR

BACKGROUND OF THE INVENTION

The present invention relates to a sensor for measuring the concentration of oxygen in gases such as an exhaust gas from an internal combustion engine, a method of measuring the oxygen concentration, and a method of controlling the air-fuel ratio of an internal combustion engine.

Internal combustion engines are subjected to strict control over the air-fuel ratio in order to decrease the energy cost or reduce exhaust gases.

From the viewpoint of pollution prevention, three deleterious components of exhaust gases, i.e., carbon monoxide, nitrogen oxides, and hydrocarbons, are removed with the aid of a three-way catalyst, and it is said that the catalyst performs most effectively when the air-fuel ratio is in the vicinity of the stoichiometric air-fuel ratio. Hence, there has conventionally been used a so-called concentration cell type oxygen concentration sensor which is highly sensitive to changes that occur in the oxygen concentration of an exhaust gas around the stoichiometric air-fuel ratio.

An exemplary system for controlling the air-fuel ratio of an internal combustion engine using the concentration cell type oxygen concentration sensor will now be described with reference to a drawing.

Figure 11:
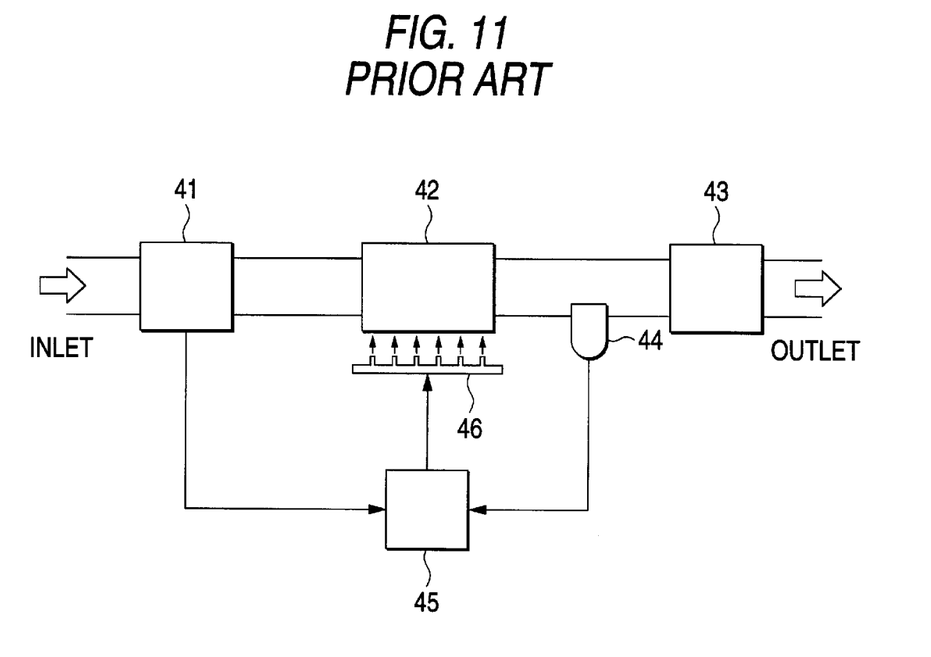
FIG. 11 shows a system for controlling the air-fuel ratio of an internal combustion engine using a concentration cell type oxygen concentration sensor.

FIG. 11 shows conceptually an internal combustion engine and an associated air-fuel control system. Shown by 41 is an air flow meter, which measures the air flow that is supplied into the internal combustion engine 42 via an inlet, with the measured value being delivered as an output to an air-fuel ratio control unit 45 (details of which will be given later). The internal combustion engine 42 uses the supplied air to burn a fuel supplied from an injector 46. The concentration of oxygen in the engine exhaust gas is measured with the concentration cell type oxygen sensor 44 and the measured value is delivered as an output to the air-fuel ratio control unit 45. The exhaust gas is thereafter passed into a three-way catalyst 43, where carbon monoxide, nitrogen oxides, and hydrocarbons are removed, and then the exhaust gas is discharged via an outlet.

In the air-fuel ratio control unit 45, the level of oxygen concentration in the exhaust gas that has been supplied from the sensor 44 is compared with the air flow level supplied from the air flow meter 41 and the fuel supply from the injector 46 into the internal combustion engine 42 is controlled in such a way that the air-fuel ratio becomes equal to a target value preliminarily set by memory means in the air-fuel ratio control unit 45.

The above-described technology is very effective for the purpose of controlling the air-fuel ratio in the neighborhood of the stoichiometric air-fuel ratio. On the other hand, attempts are being made to develop a practical lean burn system in which the air supply relative to the fuel supply into the internal combustion engine is set at higher values than in the conventional system with a view to achieving more efficient combustion and preventing incomplete combustion.

However, the conventional concentration cell type oxygen concentration sensor provides only low sensitivity during the measurement of oxygen concentrations in a combustion exhaust gas that are distant from the stoichiometric air-fuel ratio and, hence, it has been difficult to accomplish precise control over the air-fuel ratio using such oxygen concentration sensors.

In contrast, an oxygen concentration sensor of a limiting current type which is another known device capable of detecting the oxygen concentration is expected to provide satisfactory results when used in the situation just described above since it has high sensitivity in an oxygen concentration range that corresponds to the exhaust gas in the state of lean burn.

In practice, however, the output of the limiting current type oxygen concentration sensor has turned out to become unstable due to hydrocarbons and other trace components of the exhaust gas, thereby yielding measured values that are different from the actual oxygen concentration. Hence, it has been desired to develop a sensor and a method that are capable of precise measurement of the oxygen concentration of exhaust gases in the state of lean burn, as well as a method for precise control of the air-fuel ratio using such sensor and method.

SUMMARY OF THE INVENTION

The present invention has been accomplished under these circumstances and has an object of providing a sensor capable of precise measurement of the oxygen concentration of an exhaust gas in the state of lean burn.

Another object of the invention is to provide a process of producing the sensor.

Yet another object of the invention is to provide a method of measuring the oxygen concentration of a lean burnt exhaust gas using the sensor.

Still another object of the invention is to provide a method capable of precise control over the air-fuel ratio.

The method of the invention for measuring the concentration of oxygen in an exhaust gas from an internal combustion engine is implemented by using an oxygen sensor of a limiting current type adapted to remove hydrocarbons from the exhaust gas by means of a catalyst-supporting porous coating layer, a catalyst-supporting porous cap, or a catalyst-supporting porous column.

According to the present invention, an oxygen sensor of a limiting current type which is suitable for the measurement of oxygen concentration of an exhaust gas in the state of lean burn can be operated with reduced effects of hydrocarbons on the sensor output and this enables more precise control over the air-fuel ratio.

DETAILED DESCRIPTION OF THE INVENTION

A sensing element of an oxygen sensor of a limiting current type will now be described with reference to drawings.

Figure 1:
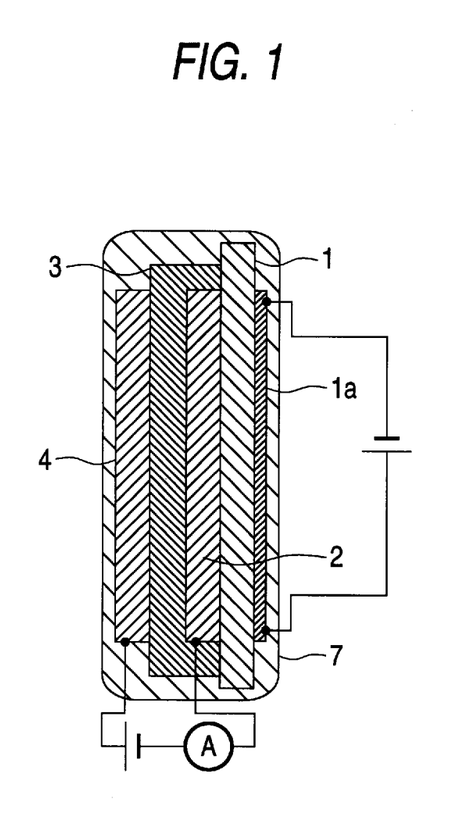
FIG. 1 shows a cross section of the sensing element of an oxygen sensor of a limiting current type.

FIG. 1 is a cross section (as a model) of the sensing element of the oxygen sensor of a limiting current type. A porous alumina substrate 1 has a platinum heater 1a and limits the rate of oxygen gas diffusion. A platinum cathode 2, a zirconia solid electrolyte layer 3 and a platinum anode 4 are formed on the porous alumina substrate 1 in the order written (these components make up the "essential part of the sensing element").

The sensing element is surrounded by a porous coating layer 7 which protects its essential part. The coating layer 7 which is formed of an alumina-based coating agent, has such high gas permeability that the gas to be measured is supplied adequately into the essential part of the sensing element which is enclosed with the coating layer 7. The heater 1a is connected to a power supply and holds the sensing element at a temperature suitable for ion conduction through the solid electrolyte.

If a voltage is applied to between the anode 4 and the cathode 2 of the sensing element of the construction described above, the ambient oxygen gas is forced through the porous alumina substrate 1 by the oxygen pumping action of the sensor to reach the cathode 2. The oxygen gas is then converted to oxygen ions at the cathode 2 and passes through the solid electrolyte layer 3, typically made of stabilized zirconia, by ion conduction to reach the anode 4. The oxygen ions are then reverted to oxygen gas. The movement of oxygen ions causes a current flow from the anode 4 to the cathode 2.

Figure 2A:
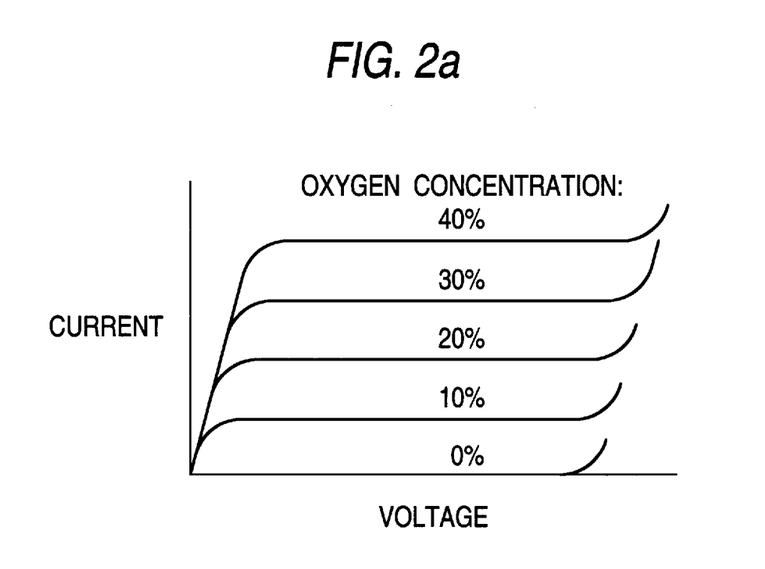
FIG. 2a is a graph illustrating the limiting current.
Figure 2B:
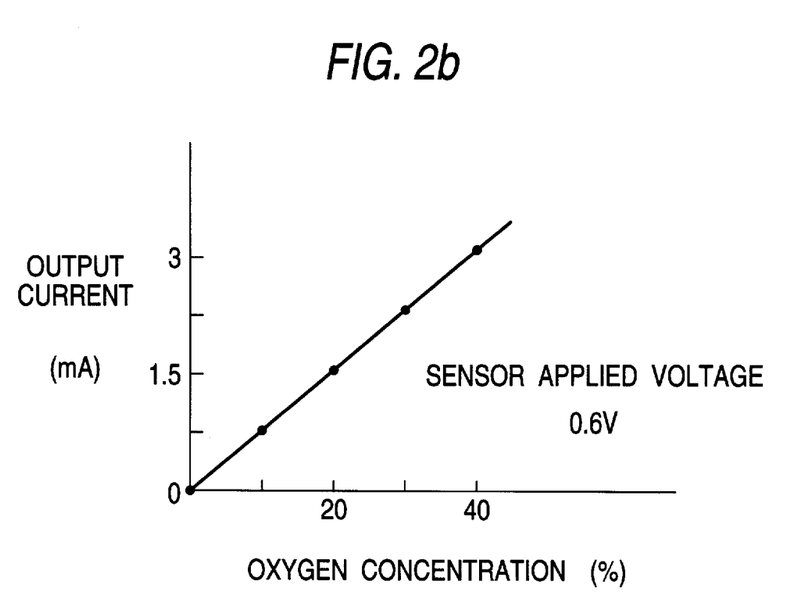
FIG. 2b is a graph showing an exemplary output characteristic of the oxygen sensor of a limiting current type.

It should be noted here that the rate of supply of oxygen gas to the cathode 2 is limited by the porous substrate 1, so that the output current of the sensor is constant in a specified voltage range (see FIG. 2a) and known as the limiting current. The value of the limiting current corresponds to the concentration of the oxygen gas around the sensor (see FIG. 2b), so that the oxygen concentration can be detected by measuring the output current of the sensor.

If the exhaust gas to be analyzed is in the state of lean burn, the output and the time-dependent stability of the sensor are greatly affected by hydrocarbons in the exhaust gas. However, since the exhaust gas contains residual oxygen gas in excess of the hydrocarbons, it is very effective to perform a catalytic oxidation method before the exhaust gas reaches the interface of the sensor electrode so that the hydrocarbon gases are removed by being reacted with the residual oxygen under the presence of a catalyst.

In the catalytic oxidation method, oxygen is also consumed together with the removal of hydrocarbons but this will cause no adverse effects on the measured values of the air-fuel ratio because, as already noted, the exhaust gas in the state of lean burn contains a sufficient amount of oxygen compared with the residual hydrocarbons.

In the catalytic oxidation method mentioned above, various catalysts, or substances having catalytic activity to oxidize hydrocarbons, such as platinum, palladium, rhodium, and iridium may be born on supports of comparatively large surface areas such as activated carbon, zeolite, silica gel, and alumina. The catalysts may be used either individually or in admixtures. Instead of being born on the supports, the fine particles of the catalysts may be dispersed in the supports. However, considering the presence of oxygen in the exhaust gas, the high operating temperatures and the durability required for prolonged use, the preferred support is alumina or a porous material containing alumina as the main component.

The catalysts on supports may be in a particulate form which can be packed into a column or the like or, alternatively, they may be used after being shaped into a tabular form. For shaping, customary methods such as sintering may be employed.

The catalyst-supporting porous alumina coating layer can be formed, for example, by adding a catalytic component or its precursor to a coating agent used for forming the coating layer 7. Alternatively, a porous alumina coating layer is first formed around the sensing element and the assembly is impregnated with a catalytic component or its precursor by immersion in a solution containing them and, if necessary the assembly is thereafter dried or subjected to an activation treatment. The term "precursor" as used herein refers to those substances which are converted to catalysts by suitable treatments such as chemical and heat treatments.

Figure 3:
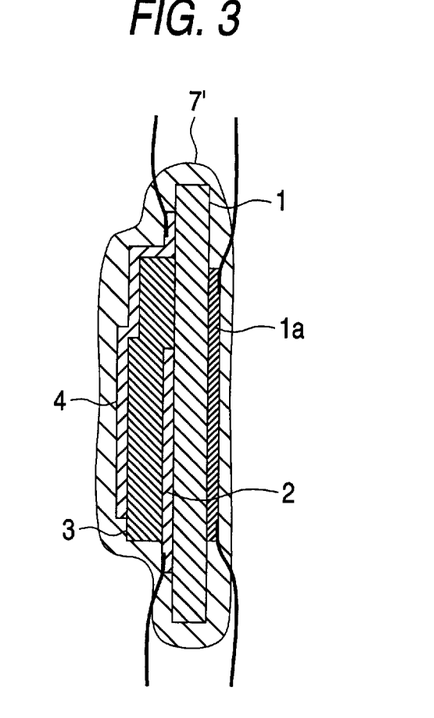
FIG. 3 shows a cross section of the sensing element of an oxygen sensor of a limiting current type which has a catalyst-supporting porous coating layer.

A cross section of the thus formed sensing element is shown in FIG. 3. Shown by 7' is the catalyst-supporting porous coating layer.

If the catalytic component to be used has electrical conductivity as in the case of platinum, rhodium, iridium, or ruthenium, these catalysts are desirably supported in amounts of not more than 50 wt % with respect to the total weight of the coating layer, in order to prevent a shorting trouble. In this case, it is preferred to use a porous alumina coating layer having a thickness of from 50 $\mu$m to 2 mm, a porosity of from 2% to 40%, and a pore size of from 0.02 $\mu$m to 1.2 $\mu$m since this contributes to the fabrication of a sensor that is less susceptible to hydrocarbons and which yet has sufficient sensitivity to oxygen.

If desired, the coating layer may be designed as a dual system consisting of a layer of the smaller catalyst content which is in contact with the sensing element and an overlying layer of the higher catalyst content; this system eliminates the adverse effects of hydrocarbons and enables the prevention of shorting.

The oxygen sensor of a limiting current type according to the invention may have the sensing element placed within a catalyst-supporting porous alumina cap such that said sensing element will contact only the gas that has been passed through said cap. In this case, the catalyst-supporting porous alumina cap may preferably be adapted to have a thickness of from 0.5 mm to 2 mm, a porosity of from 2% to 40%, and a pore size of from 0.02 $\mu$m to 3 $\mu$m since this contributes to the fabrication of a sensor, the output of which is less susceptible to hydrocarbons and which yet has sufficient sensitivity to oxygen.

In another case, a column packed with catalyst-supporting alumina may be provided upstream of the sensing element; if the column is packed with catalyst-supporting porous alumina having a particle size of from 30 $\mu$m to 50 $\mu$m, it has preferably a height of 1 mm or more and a cross-sectional area of 1 mm$^2$ or greater since this contributes to the fabrication of a sensor that is less susceptible to hydrocarbons and which yet has sufficient sensitivity to oxygen.

In the case of a sensor having the catalyst layer provided some distance away from the sensing element as in the case described in the preceding paragraph and if the temperature of the exhaust gas being supplied into the catalyst is lower than the temperature suitable for the removal of hydrocarbons, the catalyst or the exhaust gas is heated by suitable means such that it is set at an optimal temperature for achieving complete removal of hydrocarbons prior to measurement. In the above-described case of a sensor having a catalyst-supporting alumina packed column provided upstream of the sensing element, the catalyst column is desirably heated in the temperature range of 200° to 900° C. before it is put to service.

It is essential for the purposes of the invention that the height (thickness) of the catalyst layer should be adjusted to provide a sufficient time of contact with the oxidation catalyst, thereby ensuring that there will be no hydrocarbons present in the gas to be supplied into the sensor. The height required of the oxidation catalyst layer depends on the velocity of the gas that will pass through that layer and, hence, an appropriate height must be determined prior to each operation.

The oxygen sensor of a limiting current type having the oxidation catalyst layer described above is capable of measuring the oxygen concentration of an exhaust gas in the state of lean burn and on the basis of the measured value of oxygen concentration, one can control the supply of a fuel and air to an internal combustion engine using common control devices (e.g. a microprocessor, control valves, and pumps) such that an optimal air-fuel ratio is attained.

An exemplary method of performing this control will now be described with reference to FIG. 4, particularly for the case of using an oxygen sensor of a limiting current type in which a catalyst column (indicated by 13) packed with catalyst-supporting alumina having a particle size of 30 to 50 $\mu$m is provided upstream of the sensing element.

Figure 4:
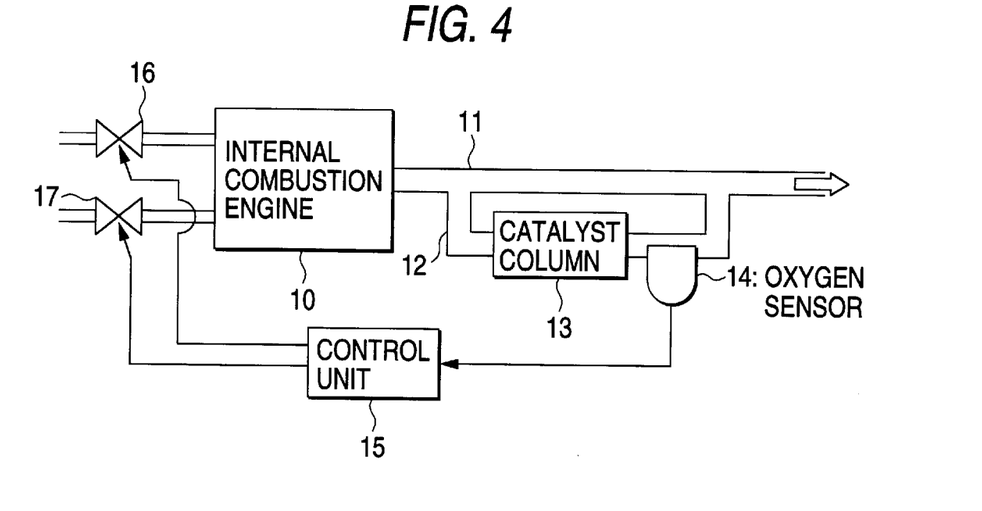
FIG. 4 is a diagram showing the concept of the air-fuel ratio control unit of the invention.

In FIG. 4, an internal combustion engine 10 is connected to a fuel supply pipe having a control valve 16 and an air supply pipe having another control valve 17. An exhaust portion 11 of the engine has a bypass line 12. The hydrocarbons in the exhaust stream flowing through the bypass line 12 are removed oxidatively as the exhaust gas passes through the catalyst column 13.

The oxygen concentration of the exhaust gas from which the hydrocarbons have been thus removed is measured with the sensing element of the oxygen sensor 14 of a limiting current type and the measured value is sent to an air-fuel ratio control unit 15. The oxygen level of the exhaust gas is compared with a value preliminarily stored in the memory means within the control unit 15 and, based on the result of the comparison, the control unit 15 controls the control valve 16 or 17 to adjust the supply of the fuel or air.

In the case just described above, the fuel and the air which are to be supplied to the internal combustion engine 10 are adjusted by valves; alternatively, in a system that employs pumps to supply the fuel and air to the internal combustion engine, the air-fuel ratio can be controlled by controlling the pumps.

In the case described above, the catalyst column 13 and the sensing element 14 are provided on the bypass 12 in order to reduce the required amount of the catalyst, that is, to remove hydrocarbons only from the volume of the gas that is required by the sensing element 14 to perform the intended measurement. If the internal combustion engine produces only a small volume of exhaust gas, the bypass line may be omitted so that the treatment for the removal of hydrocarbons is performed on all of the exhaust gas emission.

[EXAMPLE 1]

The following example concerns an oxygen sensor of a limiting current type having a catalyst-supporting porous coating layer.

The sensing element of the sensor was fabricated by the following procedure.

Figure 5A:
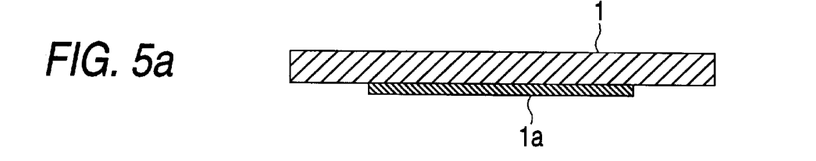
FIGS. 5a to 5f show the steps of a process for fabricating the oxygen sensor of a limiting current type which has a catalyst-supporting porous coating layer.

First, as shown in FIG. 5a, a platinum heater 1a was formed on one side of a porous alumina substrate by sputtering using a metal mask of a zigzag pattern (step 1). The sputtering conditions employed are shown in Table 1. The conditions of sputtering that was performed in subsequent steps 2 to 4 are also shown in Table 1.

TABLE 1

|  | Step 1 | Step 2 | Step 3 | Step 4 |
|---|---|---|---|---|
| Target | Pt | Pt | ZrO$_2$ + 8 mol % Y$_2$O$_3$ | Pt |
| Porous substrate | | Alumina substrate | | |
| Argon pressure | | 5 × 10$^{-3}$ Torr | | |
| Power input | 50 W | 50 W | 300 W | 50 W |
| Temperature for the heating of substrate | Not heated | Not heated | 300° C. | Not heated |
| Film thickness | 3 $\mu$m | 0.3 $\mu$m | 5 $\mu$m | 0.3 $\mu$m |
| Temperature for heat treatment | | 800° C. in air atmosphere | | |

Figure 5B:
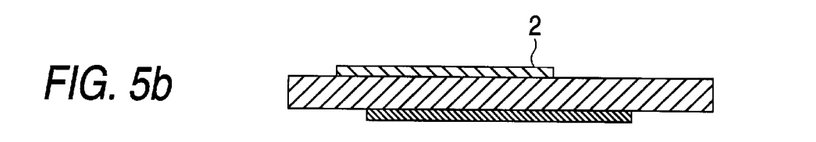

In the second step, platinum was deposited on the other side of the substrate 1 by sputtering using a metal mask for an electrode pattern to form a cathode 2 (see FIG. 5b).

Figure 5C:
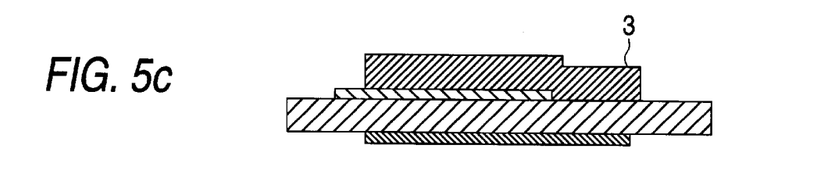

In the third step shown in FIG. 5c, a zirconium oxide layer containing 8 mol % yttrium oxide was formed on the cathode 2 by sputtering, thus forming a solid electrolyte layer 3. During step 3, connecting part of the cathode 2 was masked to ensure that no sputtering would occur in that area.

Figure 5D:
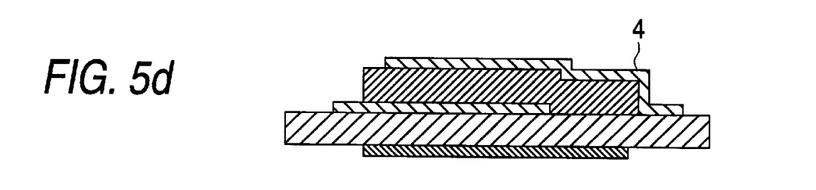

In the fourth step, a platinum anode 4 was formed on the solid electrolyte layer 3 by sputtering (see FIG. 5d). As in step 3, the area of the layer 3 near the connecting part to the cathode was masked to ensure that the anode would not be formed in that area.

Figure 5E:
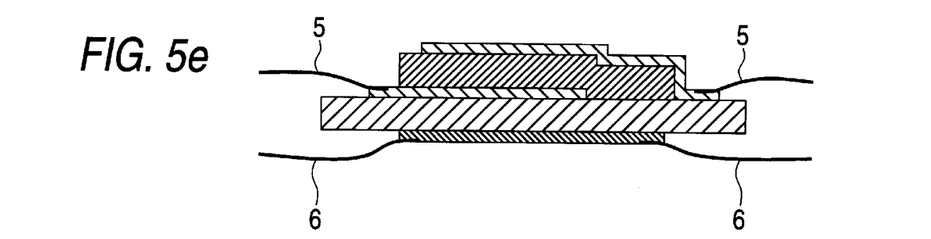

In the fifth step, signal lead wires 5 were attached to the connecting part of the cathode 2 and to the anode 4 whereas heater lead wires 6 were attached to the heater 1a (see FIG. 5e); the attachment was done with an ultrasonic bonder.

In the last sixth step, a catalyst-supporting porous coating layer 7' was formed by the following procedure. First, platinum black (particle size=200 to 300 Å) was added to an alumina coating agent (BONDEX of Nissan Chemical Industries, Ltd.) in such amounts that its final content in the support would be 0, 3, 5, 10, 15, 30, and 50 wt %; then, the ingredients were mixed to a uniform composition, thereby preparing seven types of alumina coating agent having the platinum black added in different amounts.

Figure 5F:
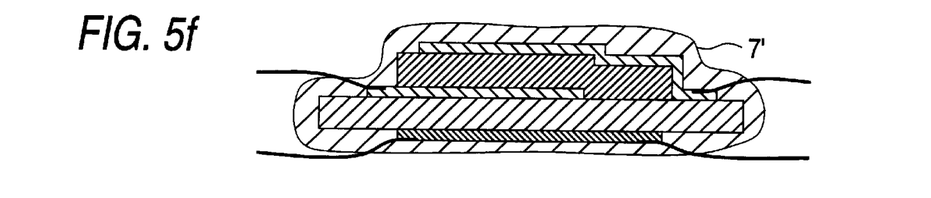

Each of these coating agents was applied in a film thickness of 0.5 mm onto the sensing element formed by the five steps described above and the applied films were left to stand at room temperature for 10 hours until they were dried. Thereafter, the assemblies were heated to 900° C. at a rate of 350° C./h and subjected to a heat treatment at a temperature of 900° C. for 30 min in the atmosphere, thereby forming the catalyst-supporting porous coating layer 7' (see FIG. 5f).

In order to evaluate the platinum black supporting coating layers, gas samples prepared by adding 0 to 2% of a hydrocarbon gas (methane or propane) to a gaseous mixture of 21% oxygen and 79% nitrogen was subjected to a test for examining the change in the output of the oxygen sensor of a limiting current type in response to the change in the concentrations of hydrocarbon gases.

In addition, the state of platinum dispersion and the size of platinum particles were investigated with EPMA (electron probe microanalyzer) and SEM (scanning electron microscope). A mercury injection method was also performed for porosity and pore size measurements.

Figure 6:
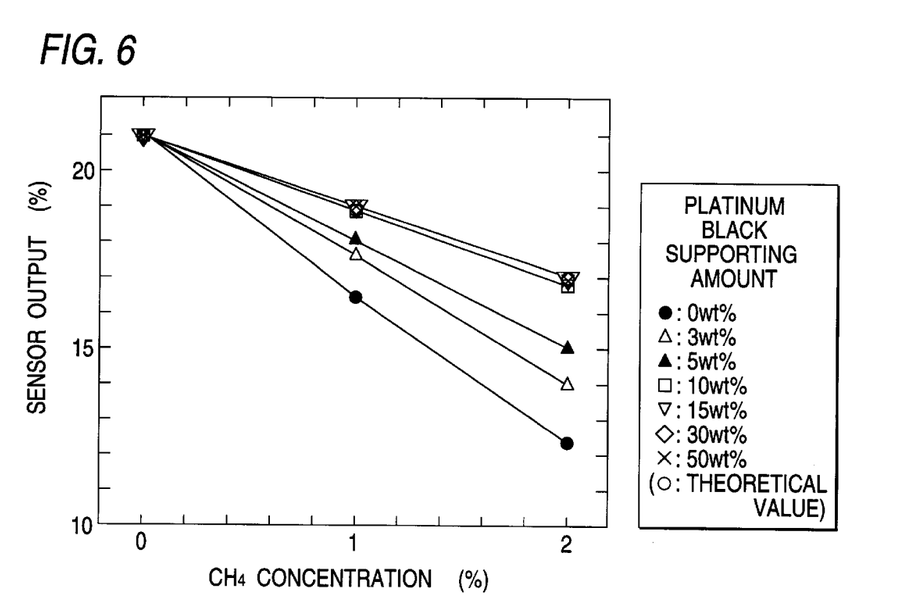
FIG. 6 is a graph showing the sensor output vs methane concentration characteristics obtained in Example 1.
Figure 7:
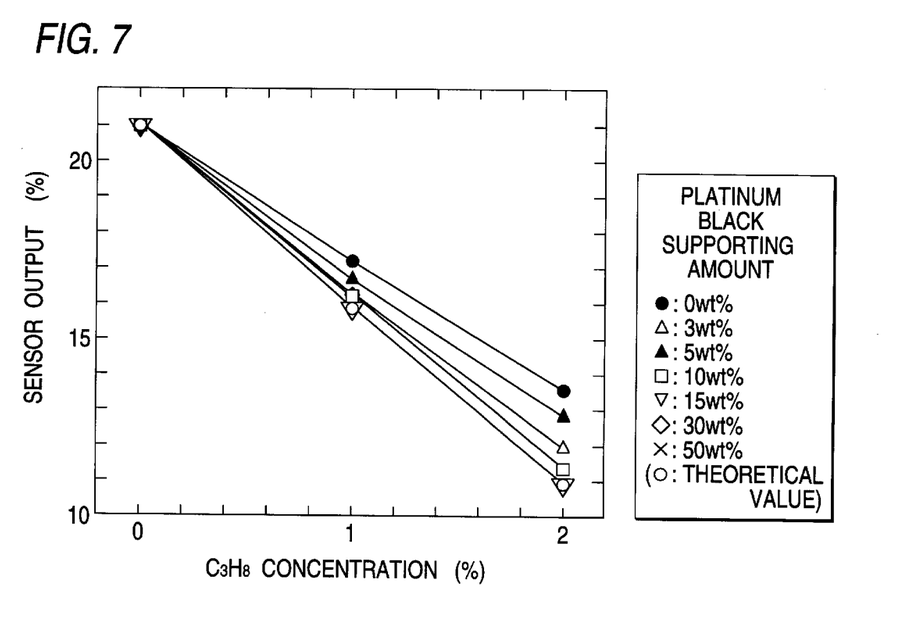
FIG. 7 is a graph showing the sensor output vs propane concentration characteristics obtained in Example 1.

The results of the respective investigations are specifically set forth below.

a) Sensor output characteristics vs the change in the concentration of hydrocarbon gas FIGS. 6 and 7 show how the output characteristics of the seven sensors supporting platinum black in different amounts were affected by changing the concentrations of hydrocarbon gases (methane and propane) from 0 to 2%.

Obviously, the addition of a hydrocarbon gas caused a marked drop in the sensor output irrespective of the gas species added. In addition, the degree of output drop varied with the type of the hydrocarbon gas added. In the presence of propane, the catalyst-supporting sensors experienced a greater output drop than the sensor supporting no catalyst, but in the presence of methane, the sensor supporting no catalyst experienced a greater output drop. The drop in sensor's output somewhat varied with the amount by which the platinum black was supported.

In FIGS. 6 and 7, the "theoretical" data (overlapping the data for 15, 30, and 50 wt % addition of the catalyst in FIG. 6) represent the sensor output for the case where the hydrocarbon gas was assumed to burn completely by reaction with oxygen gas.

As one can see from FIGS. 6 and 7, the sensor output vs the concentration of hydrocarbon gas approached the theoretical data when platinum black was added in amounts of 15 wt % and more.

b) Examination by EPMA and SEM

A section was taken of each sensor sample and the platinum dispersed in the coating layer was identified by EPMA and the size of the platinum black particles and the gap between adjacent particles were investigated by SEM. The platinum black particles were found to have grown to 1,000 to 2,000 Å as a result of the heat treatment. The gap between adjacent particles was substantially uniform in three areas, near the surface of the coating layer, in the center, and near the sensing element. The sensor output at a methane gas concentration of 2% as related to the amount of the supported platinum black and the gap between particles is shown in Table 2.

TABLE 2

| Amount of platinum black (wt %) | 0 | 3 | 5 | 10 | 15 | 30 | 50 |
|---|---|---|---|---|---|---|---|
| Gap between particles ($\mu$m) | — | 12 | 9 | 6 | 4 | 1 | 0.01 |
| Sensor output (%) | 12.3 | 14.0 | 15.0 | 16.7 | 17.0 | 17.0 | 17.0 |

As can be seen from Table 2, the sensor output was almost comparable to the theoretical value (output value: 17.0%) when the gap between adjacent platinum black particles was 6 $\mu$m and smaller. Therefore, in order that hydrocarbon gases which are inflammable gases in an ambient gas are completely oxidized with the catalyst in the sensor coating layer while said gas passes through the coating layer to reach the sensing element, the gap between adjacent catalyst particles must be 6 $\mu$m and less.

Similar results were obtained in tests that were performed on other catalysts than platinum, namely, palladium, rhodium, iridium, ruthenium, and mixtures thereof.

c) Investigation by mercury injection

An alumina coating agent containing 5 wt % platinum black was subjected to the same heat treatment as conducted in the sensor fabrication process, thereby preparing a sample for porosity and pore size measurements. Application of the mercury injection method showed that the sample had a porosity of 20% and an average pore size of 0.6 $\mu$m$\phi$.

[EXAMPLE 2]

Oxygen sensing elements of a limiting current type were fabricated by repeating the procedure of Example 1, except that no catalyst was added to the alumina coating agent. Catalyst was then added to the porous coating layers on these sensing elements by the following solution immersion method.

First, liquid impregnants containing the catalyst were prepared by dissolving 1 g of chloroplatinic acid ($H_2PtCl_6 \cdot 6H_2O$) in 20, 50, 100, and 200 ml of ethyl alcohol. The thus prepared liquid impregnants were named 20-, 50-, 100-, and 200-fold dilutions, respectively.

The sensing elements were then impregnated with these four dilutions, dried at room temperature and subjected to heat treatment, first at 300° C. for 30 min in a nitrogen atmosphere containing 1% hydrogen, then at 800° C. for 30 min in the atmosphere, thereby fabricating oxygen sensors of a limiting current type (according to the invention) which had catalyst-supporting alumina coating layers. The heat treatment at 800° C. was conducted for the specific purpose of improving the stability of sensor output.

Using the four sensor samples which had been treated for platinum supporting and a comparative sensor having an alumina coating layer that had not been impregnated with platinic acid, the platinum supporting coating layers were evaluated for their performance.

To this end, sample gases were prepared by adding 0 to 2% of a hydrocarbon gas (methane) to a gaseous mixture of 21% $O_2$ and 79% $N_2$ and the change in sensor output in response to the change in the concentration of the hydrocarbon gas was investigated. The results are shown in FIG. 8.

Figure 8:
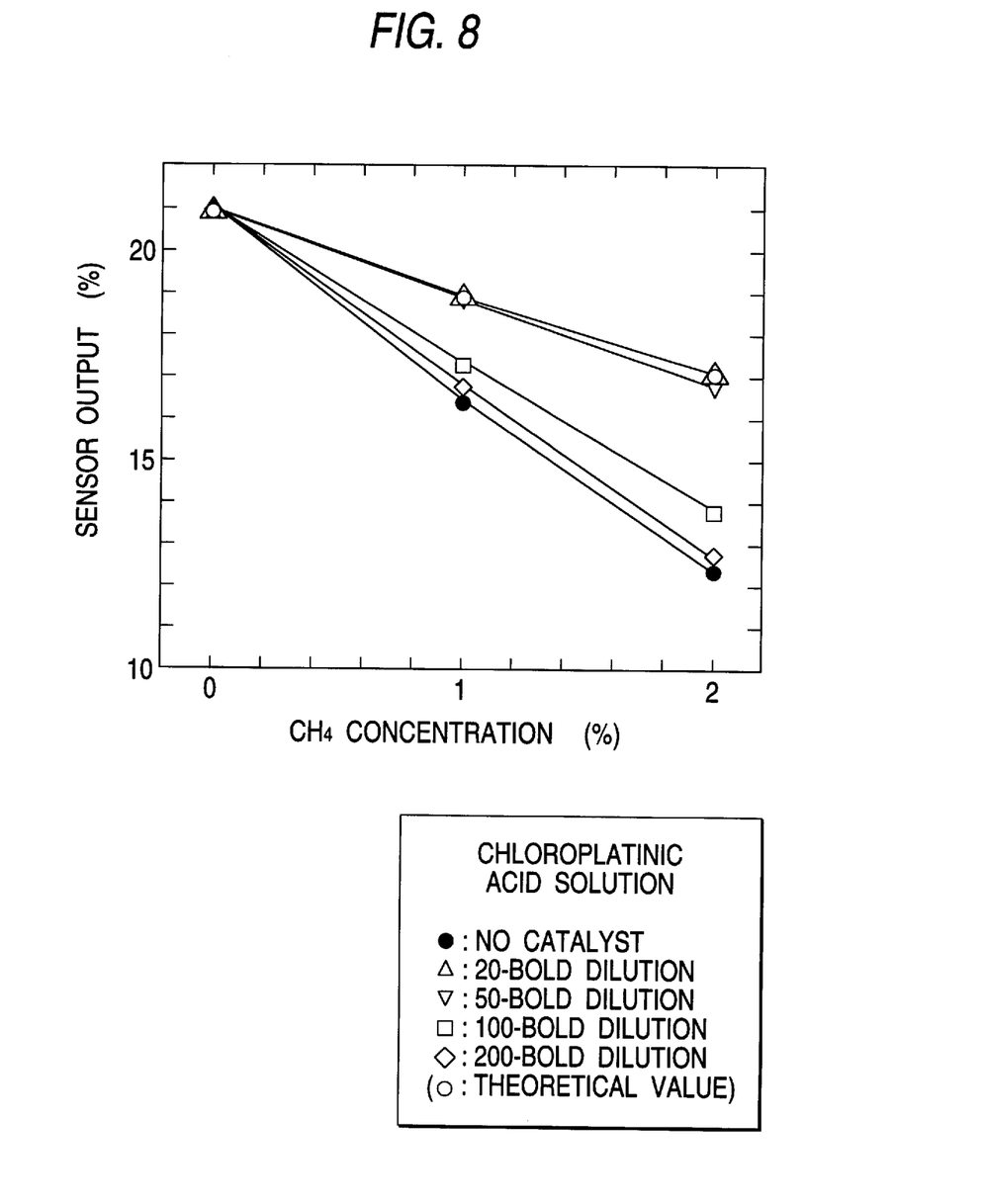
FIG. 8 is a graph showing the sensor output vs methane concentration characteristics obtained in Example 2.

As can be seen from FIG. 8, the sensors that had been treated for platinum supporting by impregnation with the 20- and 50-fold dilutions had outputs almost equal to the theoretical data. However, the output data deviated progressively from the theoretical value as the concentration of the liquid impregnant decreased and the output of the sensor treated with the 200-fold dilution was very close to the output of the comparative sensor which was not given any treatment for catalyst supporting.

A section was taken of each sensor sample and the size of the catalyst particles in the coating layer and the gap between adjacent particles were measured by examination with SEM as in Example 1. As a result, it turned out that the platinum particles had sizes of 200 to 500 Å. The dilution of the chloroplatinic acid solution used as the liquid impregnant and the gap between adjacent platinum particles as they relate to the sensor output (for a sample gas prepared by mixing 2% methane gas with a 21% $O_2$/79% $N_2$ gaseous mixture) are shown in Table 3 below.

TABLE 3

| Chloroplatinic acid solution | 20-fold dil. | 50-fold dil. | 100-fold dil. | 200-fold dil. |
|---|---|---|---|---|
| Gap between platinum black particles ($\mu$m) | 0.001 | 0.05 | 10 | 18 |
| Sensor output (%) | 17.0 | 16.8 | 13.6 | 12.7 |

Table 3 parallels with Table 2 in that it shows that the gap between platinum particles has a significant effect on the sensor output characteristics. The two tables taken together suggest that the sensor output characteristics are not influenced by the method of catalyst supporting but that the distance between catalyst particles is more critical; it can also be seen that when the catalyst particles were dispersed within the coating layer to provide gaps of no more than 6 $\mu$m, sensor output characteristics close to the theoretical data were obtained irrespective of the kind of the hydrocarbon gas present in the exhaust gas.

[EXAMPLE 3]

A bypass line was provided in the exhaust portion of a 4-cycle gasoline engine and a column installed midway of the bypass line was packed with a catalyst layer (composed of alumina particles of 50 to 30 mesh (approximately 300–600 $\mu$m) having 5% platinum supported thereon), and the sensing element of an oxygen sensor of a limiting current type was mounted downstream of the column.

The sensing element was fabricated as in Example 1, except that no catalyst was added to the coating agent. A current-voltage converter was connected to the sensing element so that it could produce voltage as an output.

The engine exhaust gas was mixed with varying concentrations of methane and the resulting change in the sensor output was investigated.

Figure 9:
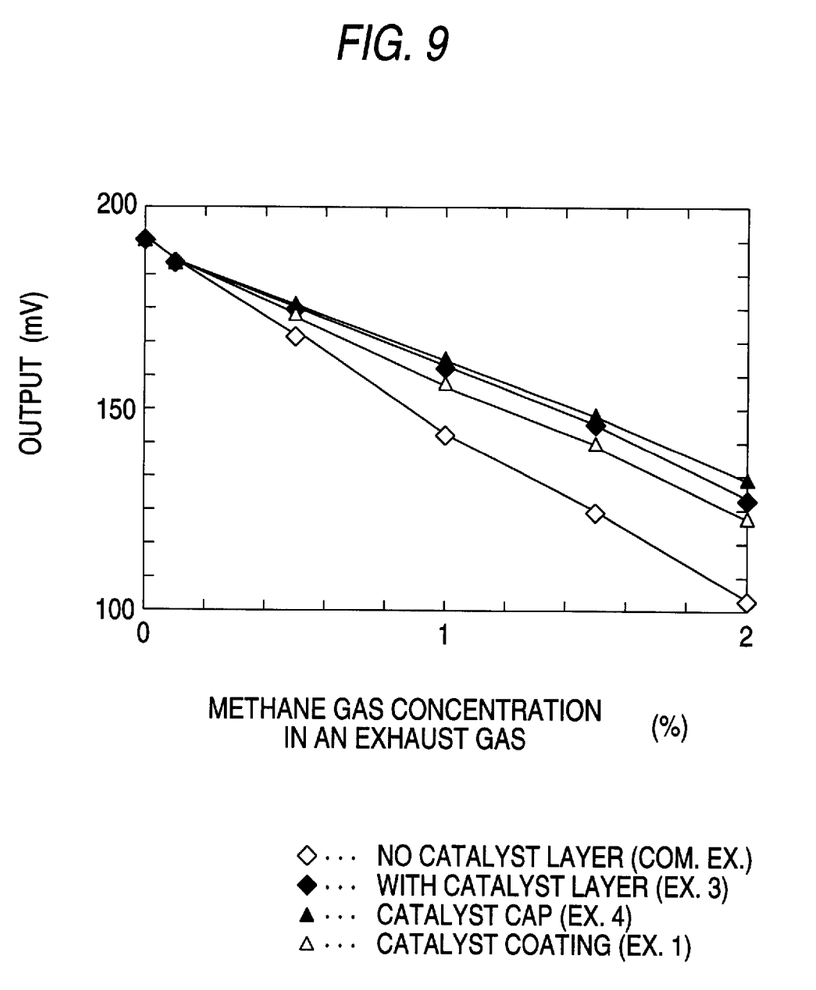
FIG. 9 is a graph showing how the concentration of methane gas in an exhaust gas influenced the sensor output in Examples 3 and 4 and in a comparative example.

The relationship between the methane concentration and the output of the oxygen sensor is shown in FIG. 9 (see the data for Example 3). A comparative experiment was conducted in the same manner except that no catalyst layer was used (i.e., the column did not contain any catalyst) and the result is also shown in FIG. 9.

As one can see from FIG. 9, the provision of the hydrocarbon removing layer upstream of the sensing element of the oxygen sensor of a limiting current type was clearly effective in preventing the sensor output from dropping on account of hydrocarbons.

[EXAMPLE 4]

In Example 3, a bypass line was provided on the exhaust pipe in order to reduce the use of the catalyst and this necessitated a substantial design alternation. Example 4 relates to the case where the provision of a bypass line is unnecessary as described below with reference to FIG. 10. Shown by 21 is an oxygen sensing element of a limiting current type having a porous coating layer supporting the same catalyst as used in Example 1. The sensing element 21 was fixed on a ceramic holder 22. Cables connecting to sensor output and other terminals were guided through a mold 23. The sensing element 21 was enclosed with a porous cap 24 (1 mm thick) which was made of sintered alumina containing 5 wt % platinum (to provide a hydrocarbon removing catalyst), thereby ensuring that the sensing element would not be directly exposed to outside air. Hence, hydrocarbons were removed from all of the gases that were brought into contact with the sensing element 21, since the gases had passed through the porous cap 24 having the hydrocarbon removing catalyst.

The porous cap 24 was warmed with a heater 25 and held at a temperature suitable for the removal of hydrocarbons. The heater 25 shown in FIG. 10 was of a plate type but it should be understood that any other forms of heater such as a coil form may be employed if they do not interfere with the passage of gases.

Figure 10:
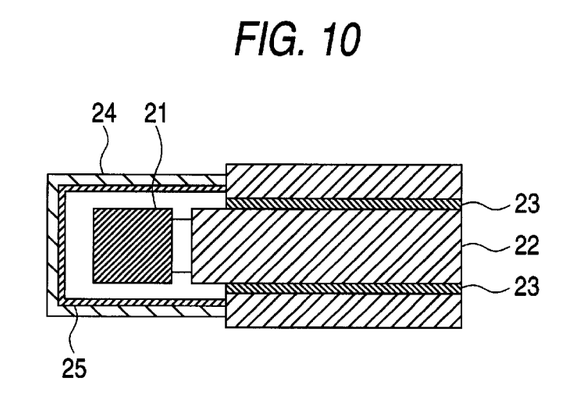
FIG. 10 shows the system used in Example 4.

The coating layer on the sensing element 21 in FIG. 10 had the catalyst supported thereon; however, due to the presence of the catalyst carrying (supporting) porous cap 24 around the sensing element, the latter may be replaced by one having a catalyst-free coating layer.

The sensor of Example 4 was installed on the exhaust pipe in the engine used in Example 3 and an exhaust gas mixed with varying concentrations of methane gas was brought into contact with the sensor as in Example 3. The sensor output vs the concentration of methane gas is profiled in FIG. 9 as data for "Catalyst cap".

As one can see from FIG. 9, the use of the sensing element of Example 4 which had porous cap 24 including the hydrocarbon removing catalyst, produced the same result as in Example 3 without providing a bypass line on the exhaust pipe.

The data for "Catalyst coating" in FIG. 9 refer to the result obtained with the sensor used in Example 1 which had a porous coating layer supporting 15 wt % platinum black; again, there was no need to provide a bypass line.

According to the present invention, an oxygen sensor of a limiting current type which is suitable for the measurement of oxygen concentration of an exhaust gas in the state of lean burn can be operated with reduced effects of hydrocarbons on the sensor output and this enables more precise control over the air-fuel ratio.

The oxygen sensor of the invention is applicable not only to control of the air-fuel ratio of internal combustion engines but also to those areas where customary combustion control is required as exemplified by gas-fueled hot water suppliers and cogeneration system.

Further, the applicability of the oxygen sensor of a limiting current type according to the invention is by no means limited to these combustion-related technologies; it can be potentially extended to medical areas for such a purpose as measuring the concentration of oxygen in anesthetic gases and other gases that contain trace organic components.

What is claimed is:

1. An oxygen sensor of a limiting current type, comprising:
    a sensing element including a substrate, a first electrode, a solid electrolyte layer, and a second electrode; and
    a porous coating layer supporting a catalyst thereon and coating said sensing element, wherein said catalyst comprises at least one element selected from the group consisting of platinum, rhodium, palladium, iridium, and ruthenium, and the content of said catalyst is 10 to 50 wt % with respect to the total weight of said porous coating layer, and particles of said catalyst are dispersed within said porous coating layer at spacings of not more than 6 $\mu$m.

2. An oxygen sensor of a limiting current type according to claim 1, wherein said porous coating layer has a thickness of from 50 $\mu$m to 2 mm, a porosity of from 2% to 40%, and a pore size of from 0.02 $\mu$m to 1.2 $\mu$m.

3. A method of measuring a concentration of oxygen in an exhaust gas from an internal combustion engine, comprising the step of using an oxygen sensor of a limiting current type according to claim 1 or 2.

4. A method of controlling an air-fuel ratio of an internal combustion engine by detecting a concentration of oxygen in an exhaust gas, comprising the steps of
    measuring the oxygen concentration of the exhaust gas using an oxygen sensor of a limiting current type according to claim 1 or 2, and
    controlling the air-fuel ratio on the basis of the measured value.

5. An apparatus for controlling an air-fuel ratio of an internal combustion engine, comprising an oxygen sensor of a limiting current type according to claim 1 or 2 provided in a bypass from an exhaust channel.

* * * * *